United States Patent
Kheradpir et al.

(10) Patent No.: US 11,766,174 B2
(45) Date of Patent: *Sep. 26, 2023

(54) TRACKED SUCTION TOOL

(71) Applicant: SYNAPTIVE MEDICAL INC., Toronto (CA)

(72) Inventors: Leila Kheradpir, Toronto (CA); Kyle Richard Dupont, Toronto (CA); Jakub Jankowski, Toronto (CA)

(73) Assignee: Synaptive Medical Inc.

( * ) Notice: Subject to any disclaimer, the term of this patent is extended or adjusted under 35 U.S.C. 154(b) by 96 days.

This patent is subject to a terminal disclaimer.

(21) Appl. No.: 17/302,354

(22) Filed: Apr. 30, 2021

(65) Prior Publication Data

US 2021/0251700 A1    Aug. 19, 2021

Related U.S. Application Data

(63) Continuation of application No. 15/732,113, filed on Sep. 21, 2017, now Pat. No. 11,020,187.

(51) Int. Cl.
*A61B 5/00* (2006.01)
*A61B 34/20* (2016.01)
(Continued)

(52) U.S. Cl.
CPC ............ *A61B 5/0077* (2013.01); *A61B 5/061* (2013.01); *A61B 5/064* (2013.01); *A61B 34/20* (2016.02);
(Continued)

(58) Field of Classification Search
CPC ......... A61B 34/20; A61B 90/36; A61B 90/39; A61B 5/0077; A61B 5/061; A61B 5/64;
(Continued)

(56) References Cited

U.S. PATENT DOCUMENTS

| RE43,526 E | 7/2012 | Morrison |
| 11,020,187 B2 | 6/2021 | Kheradpir et al. |
| (Continued) | | |

FOREIGN PATENT DOCUMENTS

| CA | 3016785 | 3/2019 |
| GB | 2570020 | 7/2019 |
| (Continued) | | |

OTHER PUBLICATIONS

Search report issued by the Intellectual Property Office of the United Kingdom in relation to corresponding GB application No. GB1815354.4 dated May 7, 2019, 5 pgs.

(Continued)

*Primary Examiner* — John Denny Li

(57) ABSTRACT

A device and method for a trackable suction tool in surgical use. A trackable suction tool involves a tubular handle with a main tube and an entrance tube extending from the main tube, a flattened section of the main tube with a suction-regulating orifice, a tip coupled with the main tube distal end and a tracking mechanism coupled with a handle proximal end. A method of tracking position of a trackable suction device involves attaching a tip to a handle in one of a plurality of fixed positions, attaching a tracking mechanism to the handle in one of a plurality of fixed positions, calibrating the position of the tip with a positional tracking system using the tracking mechanism, positioning the tracking markers in view of the positional tracking system, and tracking a position of the distal end of the tip of the suction device.

17 Claims, 11 Drawing Sheets

(51) Int. Cl.
*A61B 5/06* (2006.01)
*A61B 90/00* (2016.01)
*A61M 1/00* (2006.01)
*A61B 17/00* (2006.01)
*A61B 5/1495* (2006.01)

(52) U.S. Cl.
CPC .............. *A61B 90/36* (2016.02); *A61B 90/39* (2016.02); *A61M 1/7411* (2021.05); *A61M 1/84* (2021.05); *A61M 1/86* (2021.05); *A61B 5/1495* (2013.01); *A61B 2017/00477* (2013.01); *A61B 2017/00725* (2013.01); *A61B 2034/207* (2016.02); *A61B 2034/2051* (2016.02); *A61B 2034/2055* (2016.02); *A61B 2090/3945* (2016.02); *A61B 2090/3983* (2016.02)

(58) Field of Classification Search
CPC .......... A61B 5/1495; A61B 2034/2051; A61B 2034/2055; A61B 2034/207; A61B 2090/3945; A61B 2090/3983; A61B 2017/00477; A61B 2017/00725; A61M 1/0086; A61M 1/0047; A61M 1/008
See application file for complete search history.

(56) References Cited

U.S. PATENT DOCUMENTS

| | | |
|---|---|---|
| 2002/0107457 A1 | 8/2002 | Francese |
| 2005/0113659 A1 | 5/2005 | Pothier et al. |
| 2005/0245899 A1 | 11/2005 | Swisher |
| 2005/0260059 A1* | 11/2005 | Lees ................. F16B 41/002 411/412 |
| 2006/0241627 A1* | 10/2006 | Reo .................. A61B 17/1671 606/79 |
| 2008/0051768 A1 | 2/2008 | Stumpf |
| 2009/0099445 A1 | 4/2009 | Burger |
| 2013/0064427 A1 | 3/2013 | Picard |
| 2014/0005653 A1* | 1/2014 | Shelton, IV ........... A61B 18/14 606/205 |
| 2014/0117059 A1* | 5/2014 | Piety ..................... A45F 5/021 411/407 |
| 2014/0276004 A1 | 9/2014 | Strupeck et al. |
| 2018/0214217 A1* | 8/2018 | Rodriguez ............. A61B 90/14 |
| 2018/0368703 A1* | 12/2018 | Franjic .................. A61B 5/065 |

FOREIGN PATENT DOCUMENTS

| | | |
|---|---|---|
| WO | 95/13105 A2 | 5/1995 |
| WO | 2016058078 | 4/2016 |
| WO | 2016/116843 A1 | 7/2016 |
| WO | 2017/051224 A1 | 3/2017 |

OTHER PUBLICATIONS

Search report issued by the Intellectual Property Office of the United Kingdom in relation to corresponding GB application No. GB1815354.4 dated Jan. 26, 2022, 2 pgs.

* cited by examiner

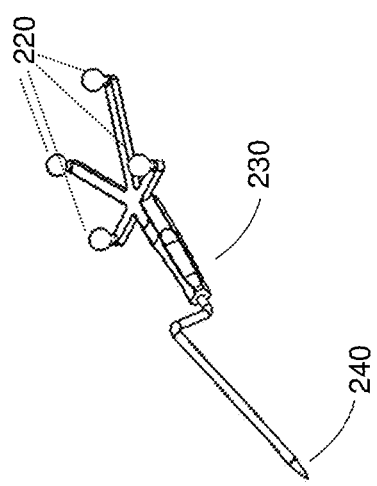
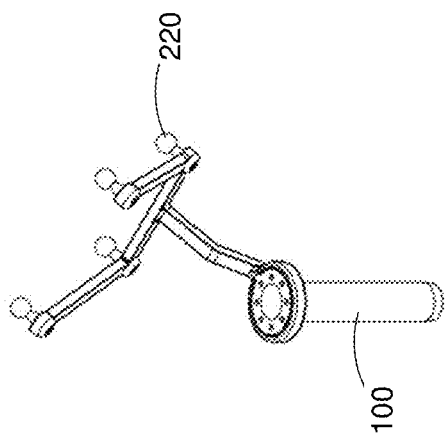
FIG. 2

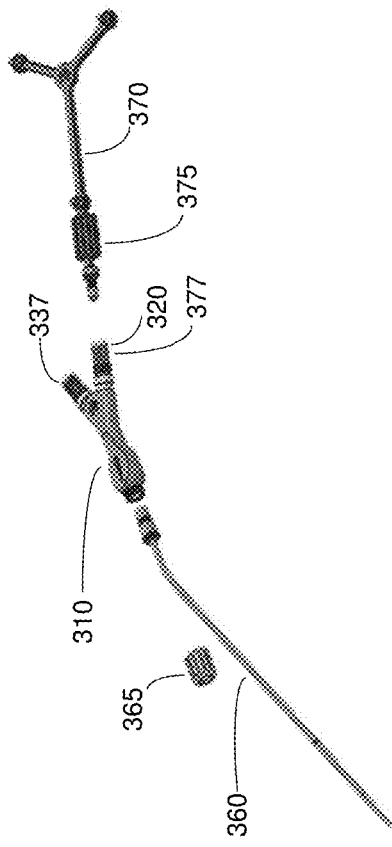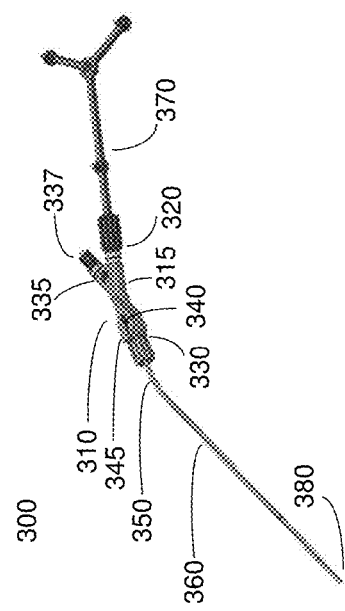
FIG. 3

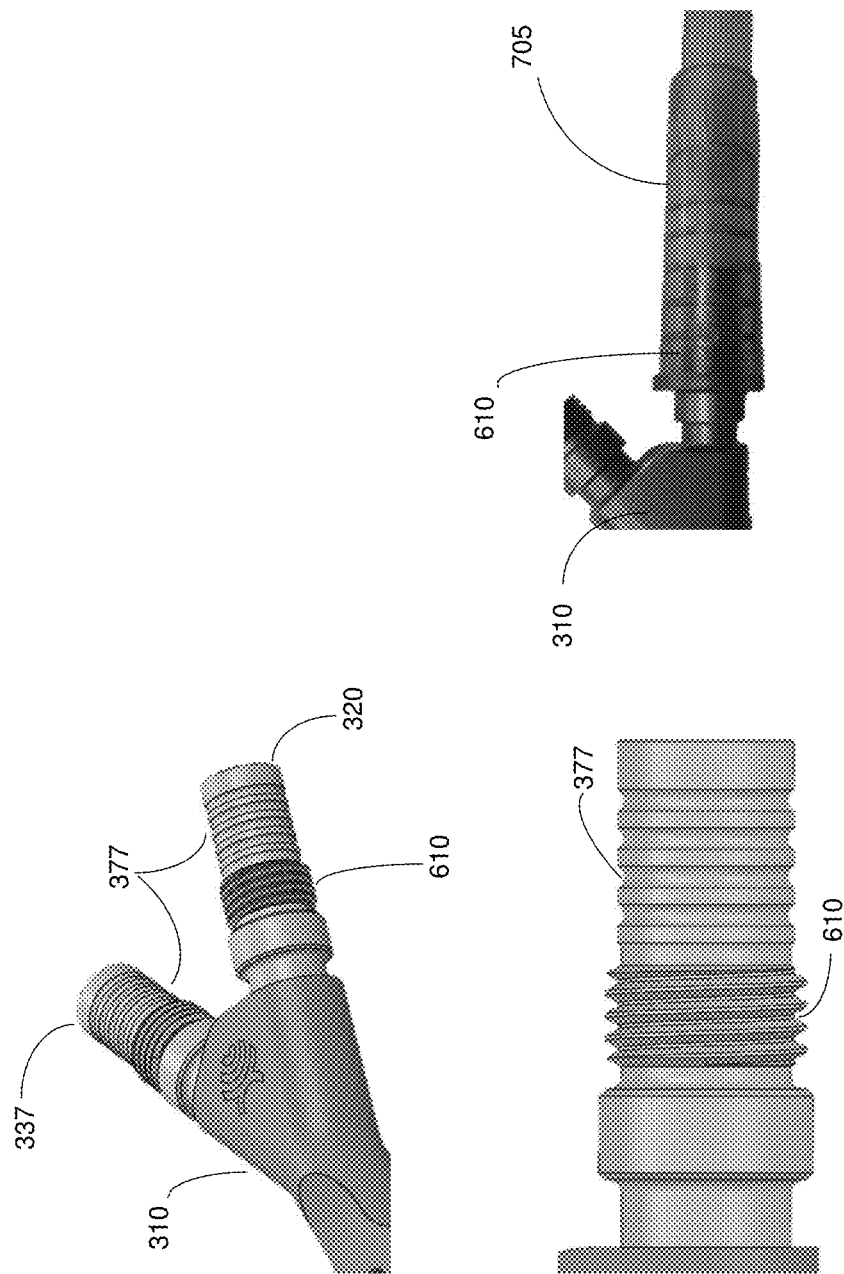

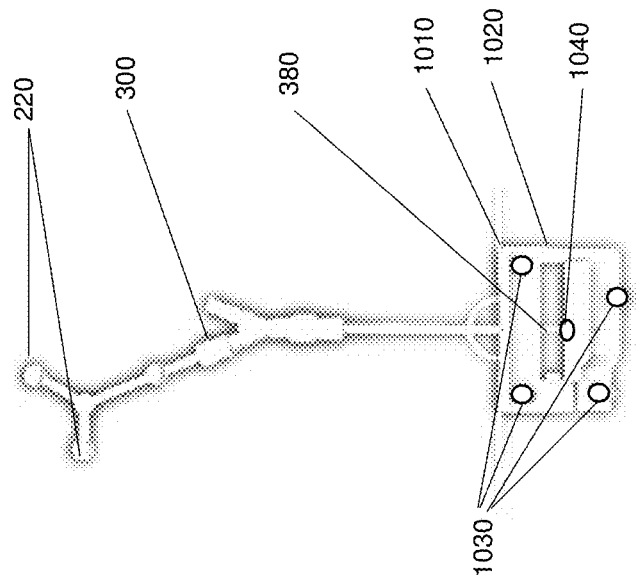
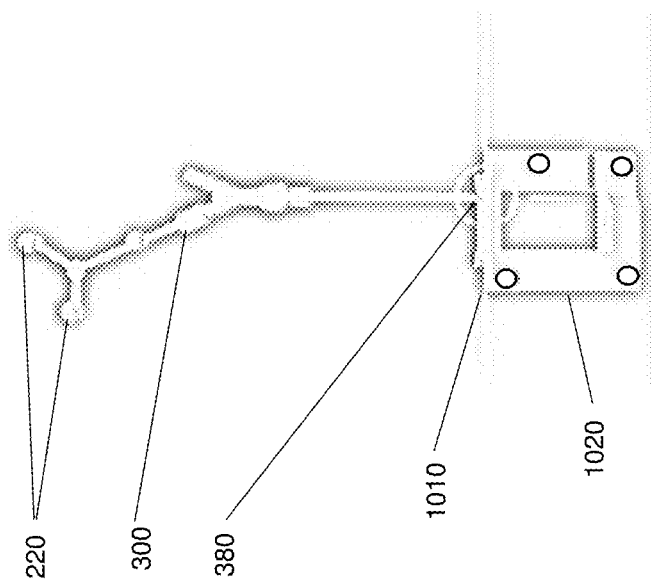
FIG. 10

TRACKED SUCTION TOOL

CROSS-REFERENCE TO RELATED APPLICATION(S)

This document is a continuation application which claims the benefit of, and priority to: U.S. patent application Ser. No. 15/732,113, filed on Sep. 21, 2017, entitled "TRACKED SUCTION TOOL," which is incorporated herein by reference in its entirety.

FIELD

The present disclosure relates to image guided medical procedures using surgical instrument tracking and, more specifically, to a tracked suction tool.

BACKGROUND

Surgical procedures have been greatly assisted by the implementation of navigation systems. Navigation systems assist in surgery by providing previously acquired imaging information, such as magnetic resonance imaging, during surgery to visualize tissue morphology and locate target areas. Navigation systems are used to track surgical instruments and their location within the tissue during surgery, typically incorporating information from previously acquired imaging data.

As an example, minimally invasive brain surgery incorporates navigation systems to map a target area for surgical resection and access the target area with minimal damage to healthy brain tissue. Corridor-based, or port-based, surgery is a minimally invasive neurosurgical procedure allowing a surgeon to perform a surgical procedure involving tumor resection in which the residual tumor is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

One aspect in minimizing trauma to intact brain matter is to track the location of surgical tools within the tissue by providing the surgical tool with a tracking device. By tracking a surgical tool, its insertion is guided within the tissue with minimal impact to healthy tissue; and the tool can be positioned correctly to serve its purpose. The tool may be tracked by overlaying a map of its position over a previously acquired or real-time imaging of the tissue. Likewise, other navigated procedures, such as spine, ENT (ear nose throat), orthopedic, and cardiac procedures benefit from surgical tools having a tracking device.

A navigation system typically includes a tracking device or object marker on the surgical tool and a detector to detect the position of the tracking device. In optical navigation systems, object markers can be light emitting diodes (LEDs), reflective stickers, unique structures and patterns or glass spheres, which utilize optical detectors. Alternatively, object markers can utilize electromagnetic (EM) or radio frequency (RF) signals, which are detected by antennas. Optical detectors require a line-of-sight between the object marker and detector during operation, but are not subject to noise and distortion from environmental influences that electrical detection and emission systems are subject.

In some cases, incorporating a tracking device on a surgical instrument can be difficult, especially on instruments with flexible portions or with multiple configurations. For example, if the tracking device is positioned in a handle or proximal region of the instrument and the distal tip moves or is moved relative to the handle, the distal tip can no longer be accurately tracked. Electromagnetic navigation systems have partly overcome the difficulty of tracking flexible tips and multiple configurations by using a flexible membrane over the tip to connect the distal tracking device with the system on the handle. However, this does not overcome the problem of multiple configurations in which the tip is swiveled about the handle or when the tip is exchangeable.

An important surgical tool is a suction device, which can be used for tissue retention, resection and removal of fluids. A suction device typically includes a handle portion and tip portion. The tip portion can be any one of multiple configurations, such as different lengths, angles and diameters, and may be removable so it can be swapped out to provide the most appropriate configuration for the surgical procedure. The multiple configurations of the tip present challenges to tracking the distal end of the tip through a tracking device on the handle, because the relative positions of the distal end of the tip and handle are different for each configuration.

SUMMARY

The present disclosure attempts to solve the foregoing problem by providing a suction device that is trackable over multiple configurations and exchangeable tips. An object of the present disclosure is to provide methods and devices for tracking suction tools using surgical navigation systems or positional tracking systems. Thus, by one broad aspect of the present disclosure, a tracked suction device is provided for use in a medical procedure comprising: an elongated tubular handle with a central passage, a main tube having a first proximal end, a distal end, and a flattened section with a suction-regulating orifice communicating with the central passage, and an entrance tube extending from the main tube having a second proximal end; an elongated tip, having a hollow tubular body, a tip distal end, and a tip proximal end detachably coupled with the main tube distal end; and a tracking mechanism detachably coupled with the handle first or second proximal end, for tracking the tip distal end, wherein the flattened section of the main tube lies in a plane defined by the main tube and the entrance tube, and the handle first and second proximal ends may be coupled with the tracking mechanism or a suction hose.

By another broad aspect of the present disclosure, a method is provided for tracking the position of a tracked suction device in a medical procedure, comprising: attaching a tip to a handle in one of a plurality of fixed positions; attaching a tracking mechanism to the handle in one of a plurality of fixed positions; calibrating the position of the tip distal end with a positional tracking system using the tracking mechanism; positioning the tracking markers of the tracked suction device in view of the tracking source (optical camera) of the positional tracking system to be tracked; and tracking a position of the distal end of the tip of the suction device.

A further understanding of the functional and advantageous aspects of the disclosure can be realized by reference to the following detailed description and drawings.

BRIEF DESCRIPTION OF THE DRAWINGS

FIG. 2 is a diagram illustrating perspective views of tracked instruments, in accordance with example embodiments of the present disclosure.

FIG. 3 is a diagram illustrating an assembled perspective view and an exploded perspective view of a trackable suction device, in accordance with example embodiments of the present disclosure.

FIG. 6 is a diagram illustrating a perspective view and a side view of attachment fittings for attaching a handle to a suction hose and tracking device, in accordance with example embodiments of the present disclosure.

FIG. 7 is a diagram illustrating a side view of a suction hose coupled with a handle, in accordance with example embodiments of the present disclosure.

FIG. 10 is a diagram illustrating a side view and a perspective view of a tracked instrument, as shown in FIG. 3, inserted into a calibration apparatus, in accordance with example embodiments of the present disclosure.

DETAILED DESCRIPTION

Figure 1:
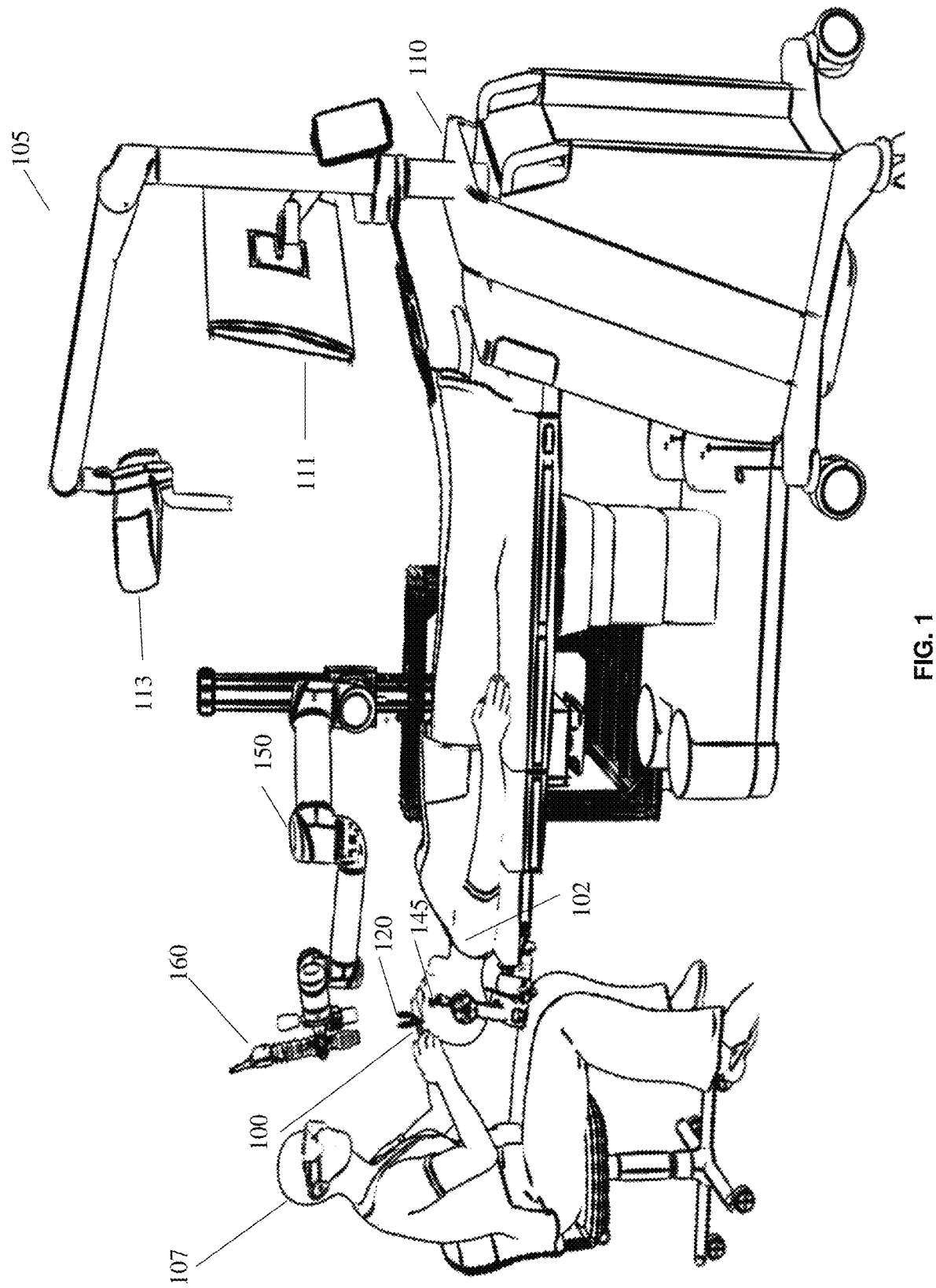
FIG. 1 is a diagram illustrating a perspective view of systems and equipment for a neurosurgical procedure, in accordance with example embodiments of the present disclosure.

Various embodiments and aspects of the present disclosure are below described with reference to details. The following description and drawings are illustrative of the present disclosure and are not to be construed as limiting the present disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps, or components are included. These terms are not to be interpreted to exclude the presence of other features, steps, or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

Understood is that, unless otherwise specified, any specified range or group is as a shorthand way of referring to each and every member of a range or group individually, as well as each and every possible sub-range or sub-group encompassed therein, and similarly with respect to any sub-ranges or sub-groups therein. Unless otherwise specified, the present disclosure relates to, and explicitly incorporates, each and every specific member and combination of sub-ranges or sub-groups.

As used herein, the term "on the order of," when used in conjunction with a quantity or parameter, refers to a range spanning approximately one tenth to ten times the stated quantity or parameter.

Unless defined otherwise, all technical and scientific terms, used herein, are intended to have the same meaning as commonly understood to one of ordinary skill in the art. Unless otherwise indicated, such as through context as used herein, the following terms are intended to have the following meanings.

As used herein, the phrase "access corridor" or "access port" refers to a cannula, conduit, sheath, port, tube, or other structure that is insertable into a subject in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein, the phrase "intraoperative" refers to an action, process, method, event, or step that occurs, or is carried out, during at least a portion of a medical procedure. Intraoperative, as defined herein, is not limited to surgical procedures and may refer to other types of medical procedures, such as diagnostic and therapeutic procedures.

As used herein, the phrase "navigation system" refers to a system that assists in surgery by providing previously acquired imaging information during surgery to visualize tissue morphology and locate target areas. Navigation systems may also be used to track surgical instruments and their location within the tissue during surgery, typically incorporating information from previously acquired imaging data.

As used herein, the phrase "positional tracking system" refers to a computer-implemented system that tracks the position of surgical instruments during surgery. A positional tracking system may be incorporated in a navigation system or may function independently of a navigation system. Where embodiments of the present disclosure refer to a navigation system, an independent positional tracking system may be alternatively used.

Embodiments of the present disclosure provide suction devices that are insertable into a subject or patient for manipulation of internal tissues, and methods of use thereof. Some embodiments of the present disclosure relate to minimally invasive medical procedures that are performed via an access port, whereby surgery, diagnostic imaging, therapy, or other medical procedures are performed based on access to internal tissue through the access port.

Several embodiments of the present disclosure seek to address the aforementioned inadequacies of existing devices and methods to support surgical procedures utilizing surgical tools.

Minimally invasive brain surgery, using access ports, is a method of performing surgery on brain tumors that were previously considered inoperable. One object of the present invention is to provide a system and method to assist in minimally invasive brain surgery. To address intracranial surgical concerns, navigation systems and robotic positioning systems have been developed for port-based surgery.

Referring to FIGS. 1 and 2, together, these diagrams illustrate a perspective view of systems and equipment for a neurosurgical procedure (FIG. 1) as well as perspective views of tracked instruments (FIG. 2), involving a port 100 comprising a cylindrical assembly comprising an outer sheath, in accordance with example embodiments of the present disclosure. The port 100 accommodates an introducer which is an internal cylinder that slidably engages the internal surface of the port 100. The introducer has a distal end in the form of a conical atraumatic tip to allow for insertion into the sulcal folds of the brain. The port 100 has a sufficient diameter to enable bimanual manipulation of surgical tools within its annular opening, such as suctioning devices, scissors, scalpels, and cutting devices, as examples.

Surgical Positional Tracking System

Still referring to FIGS. 1 and 2, together, systems, such as surgical positional tracking systems, are computer-implemented systems that track the position of surgical tools, such tools including, but not limited to, access corridors, pointers, and suction devices. The positional tracking systems track the location of surgical tools with respect to a patient and are used in conjunction with medical images of the patient and of the surgical site. An example of a surgical positional tracking system is a navigation system, as below described.

Still referring to FIGS. 1 and 2, together, the below description makes reference to the brain of a patient 102 as an example of tissue to which the techniques herein are applied. Understood, however, is that those techniques may also be applied to a wide variety of other tissues. Thus, when the brain of patient 102 is below mentioned, the brain is simply an example of the various tissues with which the systems and methods herein may be implemented. In particular, suction tools are widely used in surgery. Thus, a tracked suction device is useful in virtually all types of navigated procedures. Other examples of navigated procedures, wherein a tracked suction device would be useful, are spine surgery, ENT (ear nose throat) surgery, orthopedic surgery, and cardiac surgery.

Still referring to FIG. 1, an exemplary navigation system 105 may be used in surgery. A surgeon 107 performs surgery on a patient 102 in an operating room environment. The medical navigation system 105 comprises an equipment tower 110, supporting a computing device (not shown), such as a desktop computer, as well as one or more displays 111, coupled with the computing device, for displaying images provided by the computing device.

Referring to FIG. 1, the equipment tower 110 also supports a tracking system 113. A tracking system 113 is generally configured to track the positions of one or more tracking markers 120 mounted on the access port 100, or any of the above-mentioned surgical tools, or any combination thereof. Such markers are mounted on the patient 102, for example, at various points on the head 145 of patient 102. The tracking system 113 comprises a camera, e.g., a stereo camera, and a computing device (either the same device as above-mentioned or a separate device) configured to locate the tracking markers in the images captured by the camera and determine the spatial positions of those markers within the operating theatre. The spatial positions are provided by the tracking system 113 to the computing device in the equipment tower 110 for subsequent use.

Still referring to FIG. 1, the nature of the markers and the camera are not particularly limited. For example, the camera is sensitive to infrared (IR) light; and the tracking system 113 comprises one or more IR emitters, e.g., IR light emitting diodes (LEDs), to emit IR light on the markers. In other examples, marker recognition in the tracking system 113 is based on radio frequency (RF) radiation, visible light emitted from devices such as pulsed or un-pulsed LEDs, electromagnetic radiation, other than IR or visible light, and the like. For RF and electro-magnetic (EM)-based tracking, each object is fitted with markers having signatures unique to that object; and the tracking system 113 comprises antennae, rather than the above mentioned camera. Combinations of the above elements may also be employed.

Still referring to FIG. 1, each tracked object generally has three or more markers fixed at predefined locations on the object. The predefined locations, as well as the geometry of each tracked object, are configured within the tracking system 113; and, thus, the tracking system 113 is configured to image the operating theatre, compare the positions of any visible markers to the pre-configured geometry and marker locations, and, based on the comparison, determine which tracked objects are present in the field of view of the camera as well as what positions those objects are currently disposed.

Still referring to FIG. 1, an automated articulated arm 150, also referred to as a robotic arm or a positioning arm, carries an external scope 160, e.g., external to patient 102. The external scope 160 is positioned over the access port 100 by a robotic arm 150 and captures images of the brain of the patient 102 for presentation on the display 111. The movement of the robotic arm 150, to correctly place the external scope 160 over the access port 100, is guided by the tracking system 113 and the computing device in the equipment tower 110. The images from the external scope 160, presented on the display 111, are overlaid with other images, including images obtained prior to the surgical procedure. The images presented on the display 111 include a display of virtual models of the surgical instruments present in the field of view of the tracking system 113 (the positions and orientations of the models having been determined by the tracking system 113 from the positions of the markers, as above mentioned). Alternatively, a tracking camera is affixed to a monitor or a camera cart and directly coupled with a positional tracking system which receives and analyzes the tracking camera information.

Tracking Markers

Referring to FIG. 2 and referring back to FIG. 1, a plurality of active or passive tracking markers 220 are disposed on the port 100 and/or any medical instruments 230 to determine the location thereof using the tracking system 113 and the navigation system 105. These markers 220 may be passive reflective spheres configured for viewing by the stereo camera of the tracking system 113 to provide identifiable points for tracking. A tracked instrument in the tracking system is typically defined by a grouping of markers 220 which are used to determine the spatial position and pose of the volume of the tracked instrument in three dimensions. An exemplary tracking systems has a minimum of three spheres disposed on a tracked tool to define the instrument.

Still referring to FIG. 2 and referring back to FIG. 1, the navigation system 105 or a positional tracking system utilizes reflective sphere markers, in combination with a stereo camera system, to determine spatial positioning and pose of the medical instruments and other objects within the operating theater, in accordance to a preferred embodiment of the present disclosure. Differentiation of the types of objects and their corresponding virtual geometric volumes is determined by the specific orientation of the reflective spheres relative to one another, giving each virtual object an individual identity within the navigation system 105 or the positional tracking system, thereby allowing the navigation system 105 or the positional tracking system to identify the medical instrument 230 or other object and its corresponding virtual overlay representation. The location of the markers also provides other useful information to the navigation system 105 or the positional tracking system, such as the object's central point, central axis, orientation, and other information related to the object.

Trackable Suction Tool

Referring to FIG. 3, this diagram illustrates an assembled perspective view and an exploded perspective view of a trackable suction device, such as a suction tool 300, that is trackable during surgical procedures, in accordance with example embodiments of the present disclosure. The suction tool 300 is shown assembled in the left panel and exploded in the right panel. A hollow substantially cylindrical handle 310 comprises a main tube 315 with a first proximal end 320 and a distal end 330. The main tube 315 of the handle 310 has an entrance tube 335 extending from the main tube 315 to a second proximal end 337. The main tube 315 and the entrance tube 335, extending from the main tube 315, form a Y-shaped handle.

Still referring to FIG. 3, the handle comprises a tapered elongated slot 340, such as a tear-shaped orifice in the wall of the handle, which is widest at the proximal end and narrowest at the distal end, for controlling the amount of suction provided at the distal end of the suction tool tip. In a preferred embodiment, the handle 310 has a flattened portion 345 around the elongated slot 340, and the flattened portion lies in the plane defined by the main tube 315 and the entrance tube 335.

Still referring to FIG. 3, the handle distal end 330 comprises splines and threads for coupling with a tip, as below described in further detail. The handle first proximal end 320 and the second proximal end 337 both comprise ribs for coupling with a suction tube and splines and a thread for coupling with a tracking mechanism.

Still referring to FIG. 3, the handle distal end 330 is coupled with a proximal end 350 of a tubular hollow tip 360. The tip proximal end 350 has splines that are complementary and interlock with the splines on the handle distal end 330, thereby providing specific rotational angles of the tip 360 relative to the plane of the handle 310. The coupling is secured by a semi-captive nut 365.

Still referring to FIG. 3, a tracking mechanism 370, such as a reference tree, is coupled with the first proximal end 320 or the second proximal end 337 of the handle 310. The tracking mechanism 370 comprises tracking markers, such as reflective sphere markers. The tracking mechanism 370 has splines complementary to the splines on the first and second proximal ends of the handle, thereby providing fixed rotational positions of the tree relative to the plane of the handle 310 defined by the main tube 315 and the entrance tube 335. The coupling of the tracking mechanism 370 with the handle 310 is secured by a captive nut 375. A suction tube (not shown) is coupled with the first proximal end 320 or the second proximal end 337 of the handle 310 by sliding the suction tube over the ribs 377.

Still referring to FIG. 3, the handle 310 is used to hold and manipulate the suction tool 300, such that the tip distal end 380 is directed to the tissue, for example, for holding or resecting tissue or suctioning fluids. The tip distal end 380 is also blunted to minimize trauma to tissue while in use. The tracking mechanism 370 provides an optical marker for tracking the position of the suction tool 300 and provides position information to the tracking system 113.

Still referring to FIG. 3, the tip 360 is removed from the handle 310 by rotating and unscrewing the semi-captive nut 365 until the tip 360 is released from the threads of the distal end 330 of the handle 310. Tips of different configurations can, thereby, be exchanged and used with the suction tool. The tip 360 has one of several different lengths, angles, and diameters. Thus, by removing and replacing the tip 360, the suction tool may have different configurations. Information on the parameters for a given tip, such as tip length, diameter, and angle, is entered and stored by the computing device of the navigation system 105, and calibrated using the calibration apparatus, as shown in FIG. 10, so that, for each tip 360 used with the suction tool 300, the position of the tip distal end 380 is accurately tracked.

Tip Attachment Mechanism

Figure 4:
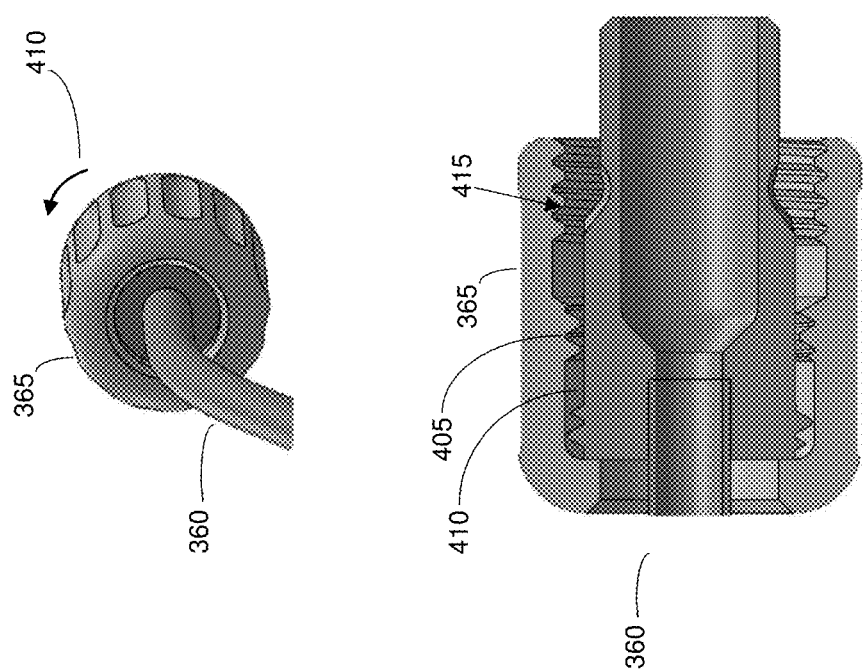
FIG. 4 is a diagram illustrating an assembled perspective and a side cross-sectional view of an attachment mechanism for attaching a tip to a handle, in accordance with example embodiments of the present disclosure.

Referring to FIG. 4, this diagram illustrates an assembled perspective and a side cross-sectional view of an attachment mechanism for attaching a tip 360 to a handle 310, in accordance with example embodiments of the present disclosure. A perspective view of the attachment mechanism securing the tip 360 and a semi-captive nut 365 is shown in the top panel; and a cross-sectional view of the attachment mechanism securing the nut 365 threaded onto the tip 360 is shown in the lower panel. The semi-captive nut 365 has two internal threads: a left-hand thread and a right-hand thread. The left-hand internal thread 405 engages the nut 365 onto the tip 360 to prevent the nut 365 from slipping from the tip 360 during assembly and disassembly of the tip 360 onto the handle distal end 330. The nut seating position 410 provides free rotation of the nut 365 around the tip 360 without removing the nut 365 from the tip 360. A larger diameter right-hand internal thread 415 is used to secure the tip 360 to the handle (not shown).

Figure 5:
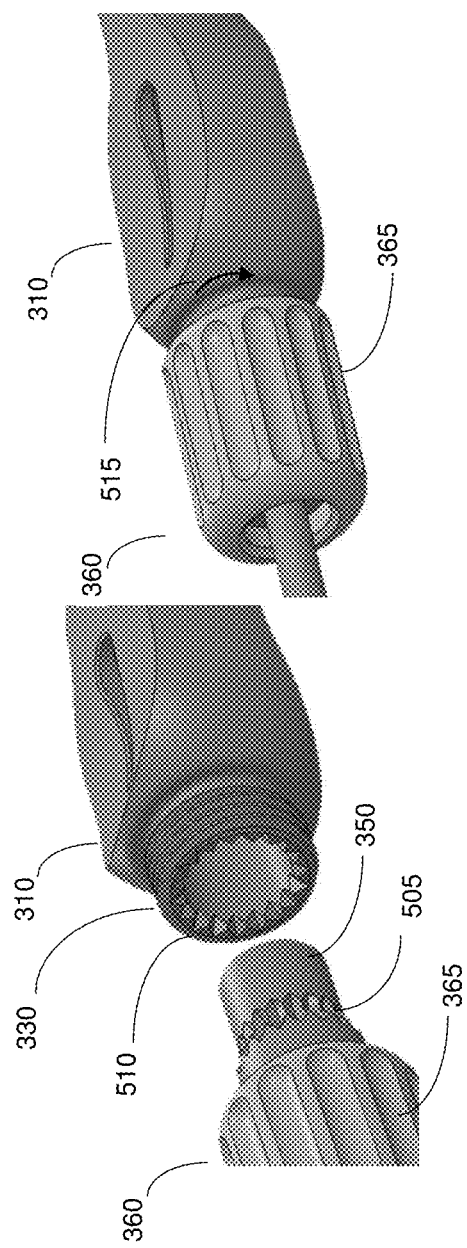
FIG. 5 is a diagram illustrating an exploded perspective view and an assembled perspective view of an attachment mechanism for attaching a tip to a handle, in accordance with example embodiments of the present disclosure.

Referring to FIG. 5, this diagram illustrates an exploded perspective view and an assembled perspective view of an attachment mechanism for attaching a tip 360 to a handle 310, in accordance with example embodiments of the present disclosure. A perspective view of the attachment mechanism for the tip 360 to the handle 310 is shown in the left panel; and the attachment mechanism securing the tip 360 on the handle 310 is shown in the right panel. External splines 505 on the tip proximal end 350 are complementary to internal splines 510 on the handle distal end 330. The tip external splines 505 fit into the handle internal splines 510 to prevent rotation and hold the tip at a fixed position after securing the tip with the nut 365. The tip and handle ends have 18 splines, thereby allowing 18 rotational positions (20° apart) of the tip around the axis of the handle.

Still referring to FIG. 5 and referring back to FIG. 4, to attach the tip 360 to the handle 310, the semi-captive nut 365 is slid onto the tip 360 until the internal left-hand thread 405 is engaged with the thread on the tip proximal end 350. The nut 365 is threaded onto the tip 360 until the tip threads sit in the seating position 410, so the nut is coupled with the tip 360 but able to freely rotate. The tip 360 is then inserted into the handle 310 fully to mate with the internal 510 and external splines 505. The nut 365 is then threaded in the opposite direction 515 onto the handle distal end 330 until the tip 360 is fully seated and secured.

Tube and Tracking Mechanism Attachment

Referring to FIG. 6, this diagram illustrates a perspective view and a side view of attachment fittings for attaching a handle 310 to a suction hose and tracking device, in accordance with example embodiments of the present disclosure. The attachment fittings comprise fittings for attaching the suction tube (not shown) or the suction hose or the tracking mechanism, such as a reference tree 370, to the handle 310. The first and second proximal ends 320, 337 of the handle 310 both comprise ribs 377 for attachment of a suction tube (not shown) and adjacent threads 610 for a tracking device nut.

Referring to FIG. 7, this diagram illustrates a side view of a suction hose, e.g., a tube 705, coupled with a handle 310, in accordance with example embodiments of the present disclosure. The tube 705 is coupled with a start of the threads for smaller tube diameters. The tube 705 is attached over the threads 610 for larger tube diameters.

Figure 8:
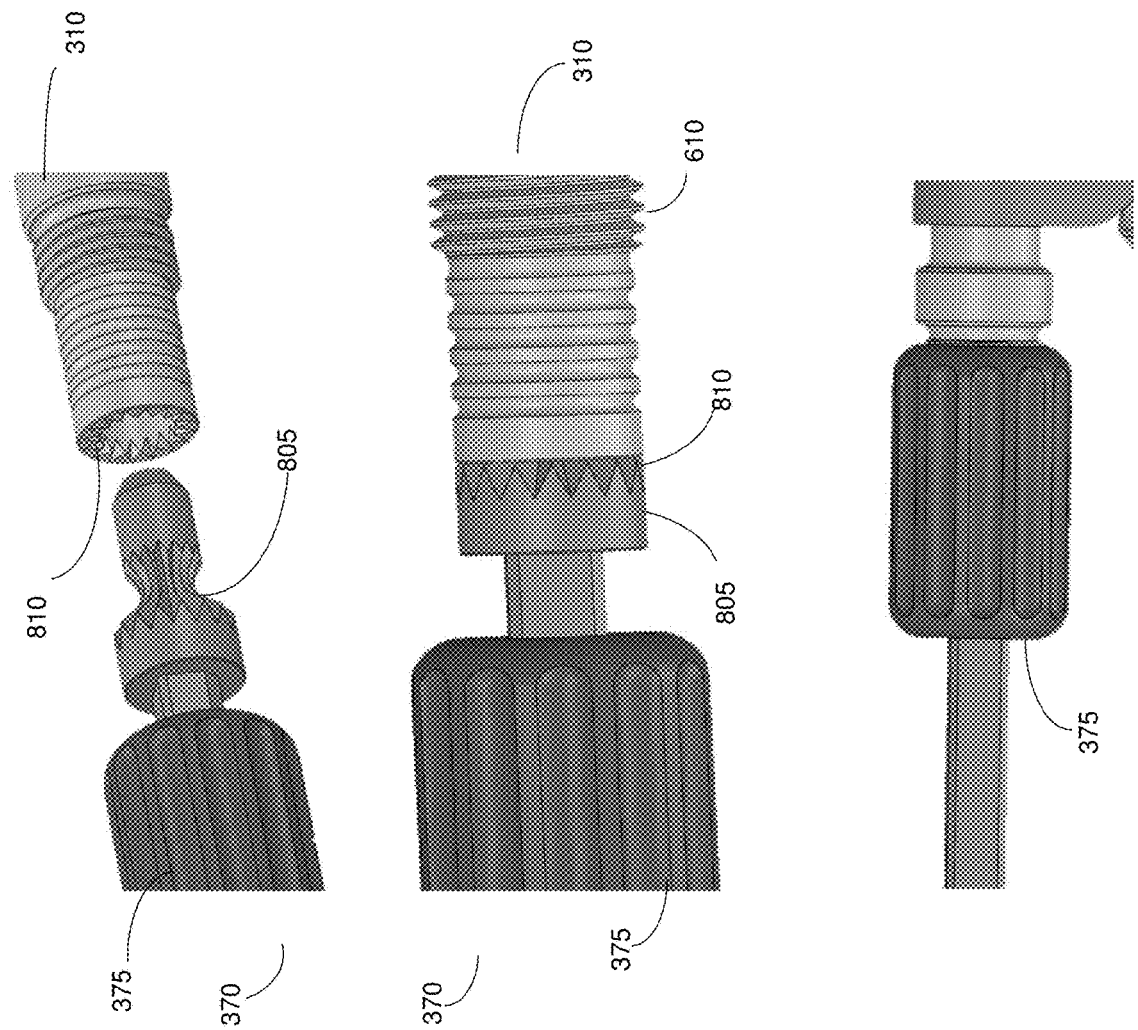
FIG. 8 is a diagram illustrating an exploded perspective view, a side assembled view, and an opposing side assembled view, of an attachment mechanism for attaching a handle to a tracking device, in accordance with example embodiments of the present disclosure.

Referring to FIG. 8, this diagram illustrates an exploded perspective view, a side assembled view, and an opposing side assembled view, of an attachment mechanism for attaching a handle to a tracking device, in accordance with example embodiments of the present disclosure. Attachment fittings for a tracking mechanism, such as a reference tree, 370, at the first and second proximal ends 320, 337 of the handle 310 are shown. The top panel of FIG. 8 illustrates an unattached tracking mechanism 370 and handle 310. The tracking mechanism end has splines 805 that fit into complementary splines 810 on the handle proximal end, which prevent rotation after the tracking mechanism is secured with the captive nut 375. In an embodiment, the tracking mechanism comprises 16 external splines and the handle comprises 16 internal splines, thereby allowing 16 rotational positions, 22.5° apart, to maximize flexibility with the tool positioning relative to the camera of the navigational system. The middle panel of FIG. 8 illustrates the tracking mechanism 370 and handle 310 with fully seated splines 805, 810 prior to threading the captive nut 375 onto the threads 610, and the lower panel of FIG. 8 illustrates the tracking mechanism and handle fully secured with the captive nut 375 screwed onto the threads.

Referring back to FIG. 3, the attachment mechanisms, as described, provide for multiple positions of the tip 360 relative to the tracking mechanism 370 around the circumference of the handle 310, thereby allowing easier use for right-hand users and left-hand users and for different positions of an angled tip without obstructing the line of sight for the tracking mechanism 370. Multiple positions of the tracking mechanism 370 are also enabled by placement on either the first and second proximal ends 320, 337 of the handle 310, and by rotating the tracking mechanism position relative to the handle 310 by locking into different spline positions. The rotatable tracking mechanism 370 affords rotation of the tracking mechanism to optimize line of sight and provide a preferred working configuration, while maintaining a fixed rotational axis of the tracking mechanism 370 relative to the plane of the handle 310 defined by the handle main tube 315 and entrance tube 335. The attachment mechanisms also allow different tracking mechanism 370 configurations to be switched for unique identification of one or more suction tools/medical instruments in the same surgical space.

Figure 9:
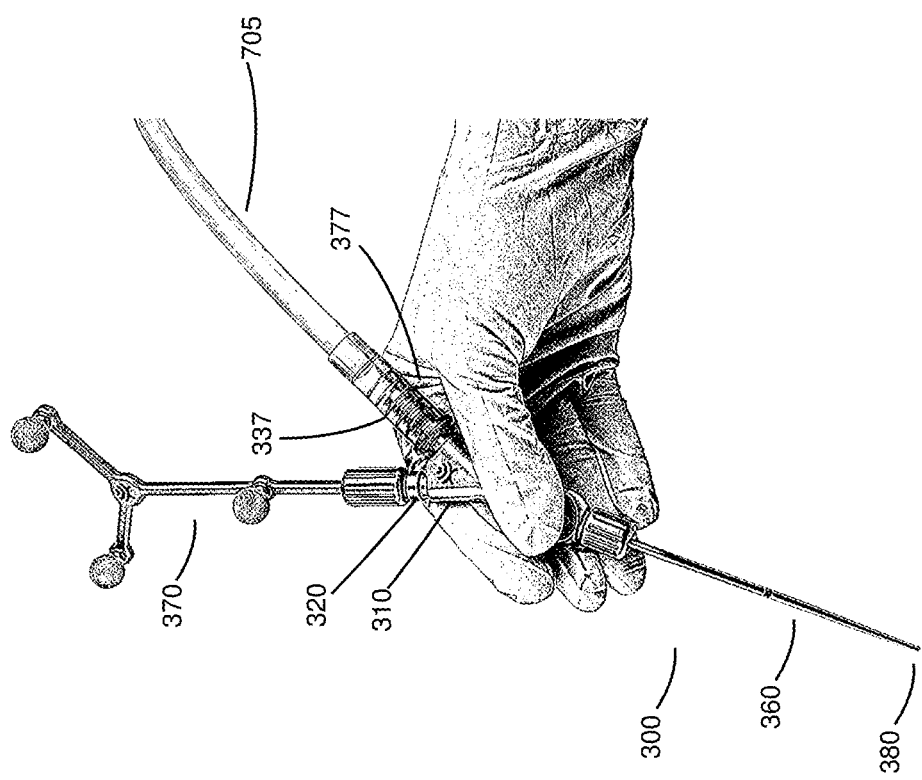
FIG. 9 is a diagram illustrating a perspective view of a trackable suction device in use, in accordance with example embodiments of the present disclosure.

Referring to FIG. 9 and referring back to FIG. 3, this diagram illustrates a perspective view of a trackable suction device in use, such as a tracked suction tool, e.g., a suction tool 300, as shown in FIG. 3, in accordance with example embodiments of the present disclosure. The suction tool 300 is held by a user 900, e.g., a surgeon, with the tracking markers 220 of the tracking mechanism 370, providing positional information of the suction tool 300 to the tracking system 113 (FIG. 1), wherein the positional tracking system or navigation system 105 (FIG. 1) is able to calculate and display the position of the suction tool tip 360 to the surgeon. The suction tool 300 is coupled with the suction tube 705 at the handle first or second proximal end 320, 337. The rib aspect 377 of the first and second proximal ends 320, 337 of the handle 310 ensures a tight and secure fit with the suction tube 705.

Still referring to FIG. 9 and referring back to FIG. 3, the suction tool 300 is registered in the positional tracking system or navigation system 105 (FIG. 1) and, prior to use, is calibrated to provide accurate registration of the tracking markers 220 (FIG. 2) with the tip distal end 380. Calibration ensures that a current configuration of the suction tool 300 is accurately registered in the positional tracking system or navigation system 105 (FIG. 1), including changes, such as different tips, adjustment of the tracking mechanism 370, user's grip of the suction tool, and deformations of the tip 360. A vacuum tube or suction tube 705 is coupled with the first and second proximal ends 320, 337 of the handle 310.

Still referring to FIG. 9 and referring back to FIG. 3, the suction tool 300 is equipped with an exchangeable hollow tip 360. The tip 360 comprises a bend between the proximal end and distal end. The bend angle comprises a range of between 60 and 180 degrees. The tip 360 is rigid or malleable. A rigid tip is distinguished from a malleable tip by an external marking to enable the surgeon to easily distinguish a tip 360 among a plurality of tips 360. The malleable tip can be further bent by the user (surgeon) during the medical procedure. The hollow tip comprises a range of length between 50 mm and 250 mm and a range of diameter between 3 and 34 FR. The above embodiments allow: a choice of which hand to use for holding the suction tool 300, specific holding angles to be attained, the reference tree 370 to be manipulated for the best view, and suction tools 300 to be customized and replaced with accuracy and minimum inconvenience.

Calibration of Tracked Medical Instrument

Referring to FIG. 10, this diagram illustrates a side view and a perspective view of a tracked instrument, such as a trackable suction tool 310, as shown in FIG. 3, inserted into a calibration apparatus 1010, in accordance with example embodiments of the present disclosure. In order to provide the dimensions of the suction tool 300, the dimensions of the suction tool 300 are registered and stored in the navigation system 105 or the positional tracking system and subsequently calibrated before use in surgery. An exemplary calibration procedure is below provided. The techniques for calibrating a tracked instrument can be found in international application CA2014051004 titled "CALIBRATION APPARATUS FOR A MEDICAL TOOL" which is incorporated by reference herein in its entirety.

Still referring to FIG. 10, the suction tool 300 and the calibration apparatus 1010 are used in conjunction with a positional tracking system, such as the medical navigation system 105. The calibration apparatus 1010 comprises a frame 1020, at least one frame tracking marker 1030 coupled with the frame 1020, and a reference point 1040 formed on the frame 1020. In one example, the reference point 1040 comprises a divot having an appropriate shape for securely receiving the distal end of the suction tool tip 380. For the purposes of this example, the reference point 1040 is referred, throughout, as a divot 1040. The divot 1040 provides a known spatial reference point relative to the frame tracking markers 1030. For example, the medical navigation system 105 has data saved therein so that the medical navigation system knows the position in space of a floor of the divot 1040 relative to the tracking markers 1030 to a high degree of accuracy. In one example, a high degree of accuracy refers to a tolerance of 0.08 mm, but any suitable tolerance may be used according to the criteria of a particular application.

Still referring to FIG. 10, in the example shown, the calibration apparatus 1010 has four passive reflective tracking spheres, but any suitable number of tracking markers 1030 may be used; and any suitable type of tracking marker 220 may be used according to the criteria of a particular application, including an active infrared (IR) marker, an active light emitting diode (LED), and a graphical pattern. When passive reflective tracking spheres are used as the tracking makers 1030, at least three tracking markers 220 are typically coupled with a same side of the frame 1020. Likewise, when a suction tool 300, having passive reflective tracking spheres, is used in conjunction with the calibration apparatus 1010, the suction tool 300 typically has at least three tracking markers 220 therewith coupled.

Still referring to FIG. 10, in the left panel, the distal end 380 of the suction tool 300 is inserted into the calibration apparatus 1010 for a reading by the medical navigation system 105. When the suction tool 300 is inserted into the calibration apparatus 1010, the position of the distal end 380 of the suction tool 300 relative to the tracking markers 220 that the medical navigation system 105 is seeing, e.g., using the camera of the tracking system 113, may be learned and saved by the navigation system 105. The distal end 380 of the suction tool 300 is then inserted onto the divot 1040 for verification of the localization of the suction tool 300. Since the medical navigation system 105 knows the precise dimensions of the calibration apparatus 1010, the medical navigation system 105 learns the dimensions of the suction tool 300. In other words, the position of the floor of the divot 1040 relative to the tracking markers 220 that the medical navigation system 105 is seeing, e.g., using the camera of the tracking system 113, is known. Other calibration devices and methods may be used to localize the distal end 380 of the suction tool 300 relative to the tracking markers 220.

Figure 11:
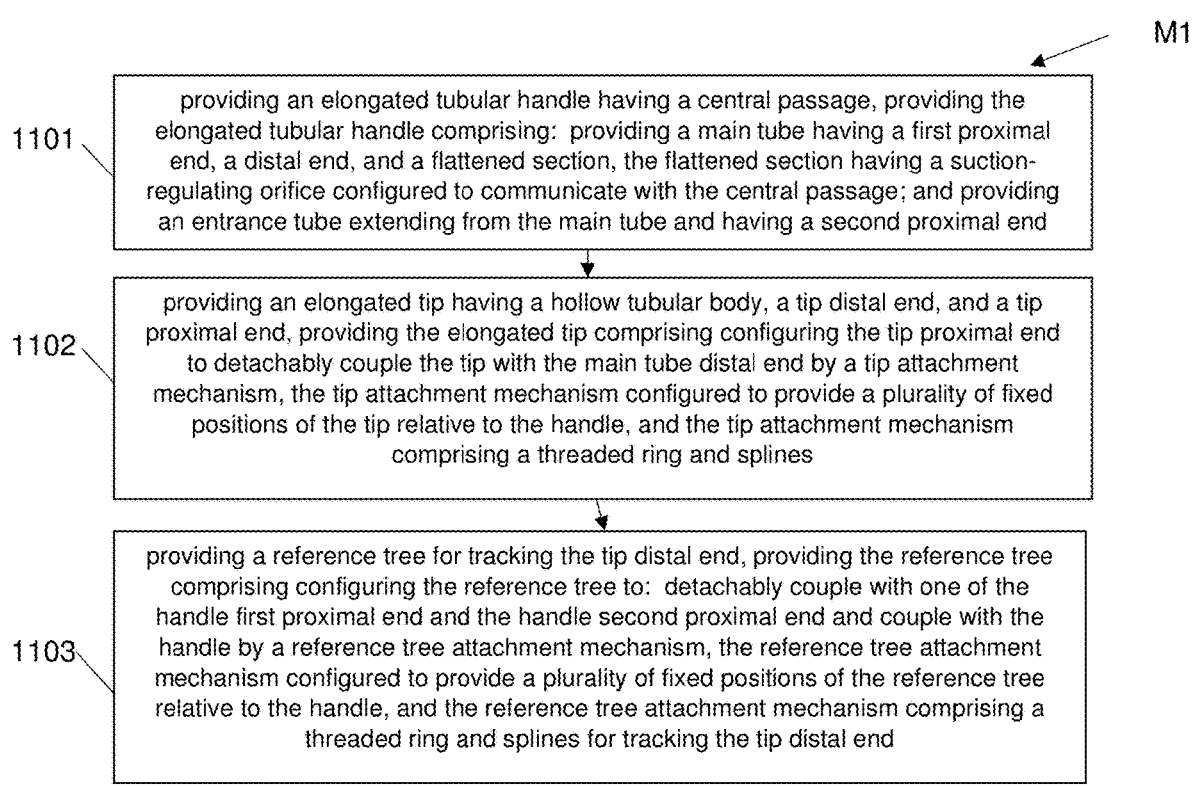
FIG. 11 is a flow diagram illustrating a method of providing a trackable suction device, in accordance with an embodiment of the present disclosure.

Referring to FIG. 11, this flow diagram illustrates a method M1 of providing a trackable suction device, e.g., a suction tool 300, in accordance with an embodiment of the present disclosure. The method M1 comprises: providing an elongated tubular handle, e.g., a handle 310, having a central passage, providing the elongated tubular handle comprising: providing a main tube having a first proximal end, a distal end, and a flattened section, the flattened section having a suction-regulating orifice configured to communicate with the central passage; and providing an entrance tube extending from the main tube and having a second proximal end, as indicated by block 1101; providing an elongated tip, e.g., a tip 360, having a hollow tubular body, a tip distal end, and a tip proximal end, providing the elongated tip comprising configuring the tip proximal end to detachably couple the tip with the main tube distal end by a tip attachment mechanism, the tip attachment mechanism configured to provide a plurality of fixed positions of the tip relative to the handle, and the tip attachment mechanism comprising a threaded ring and splines, as indicated by block 1102; and providing a reference tree, e.g., a reference tree 370, for tracking the tip distal end, providing the reference tree comprising configuring the reference tree to: detachably couple with one of the handle first proximal end and the handle second proximal end and couple with the handle by a reference tree attachment mechanism, the reference tree attachment mechanism configured to provide a plurality of fixed positions of the reference tree relative to the handle, and the reference tree attachment mechanism comprising a threaded ring and splines for tracking the tip distal end, as indicated by block 1103.

Still referring to FIG. 11, in the method M1, providing the elongated tip comprises disposing the main tube flattened section in a plane defined by the main tube and the entrance tube; and providing the elongated tubular handle comprises configuring at least one of the handle first proximal end and the handle second proximal end to couple with at least one of the reference tree and a suction tube. Configuring at least one of the handle first proximal end and the handle second proximal end to couple with the reference tree comprises configuring a plurality of threads to couple the reference tree with at least one of the handle first proximal end and the handle second proximal end. Configuring at least one of the handle first proximal end and the handle second proximal end to couple with the suction tube comprises configuring a plurality of ribs to couple the suction tube with at least one of the handle first proximal end and the handle second proximal end.

Still referring to FIG. 11, in the method M1, providing the entrance tube comprises providing the entrance tube extending from the main tube at an angle in a range of less than approximately 90°. Providing the elongated tubular handle comprises providing the handle orifice with a tear-shaped orifice. The tip attachment mechanism further comprises a plurality of complementary splines on the handle and the tip proximal end. The tip attachment mechanism further comprises a threaded semi-captive nut configured to couple the tip proximal end with the handle, wherein the threaded semi-captive nut comprises a first internal thread configured to engage the tip proximal end, a nut seating position configured to provide free rotation of the nut when the nut is engaged with the tip proximal end through the first internal thread, and a second internal thread with a larger diameter than the first internal thread configured to engage the handle, wherein the reference tree attachment mechanism further comprises at least one of: complementary splines on the handle and the reference tree; a threaded captive nut to attach the reference tree to the handle; and markers for an optical navigation system.

Figure 12:
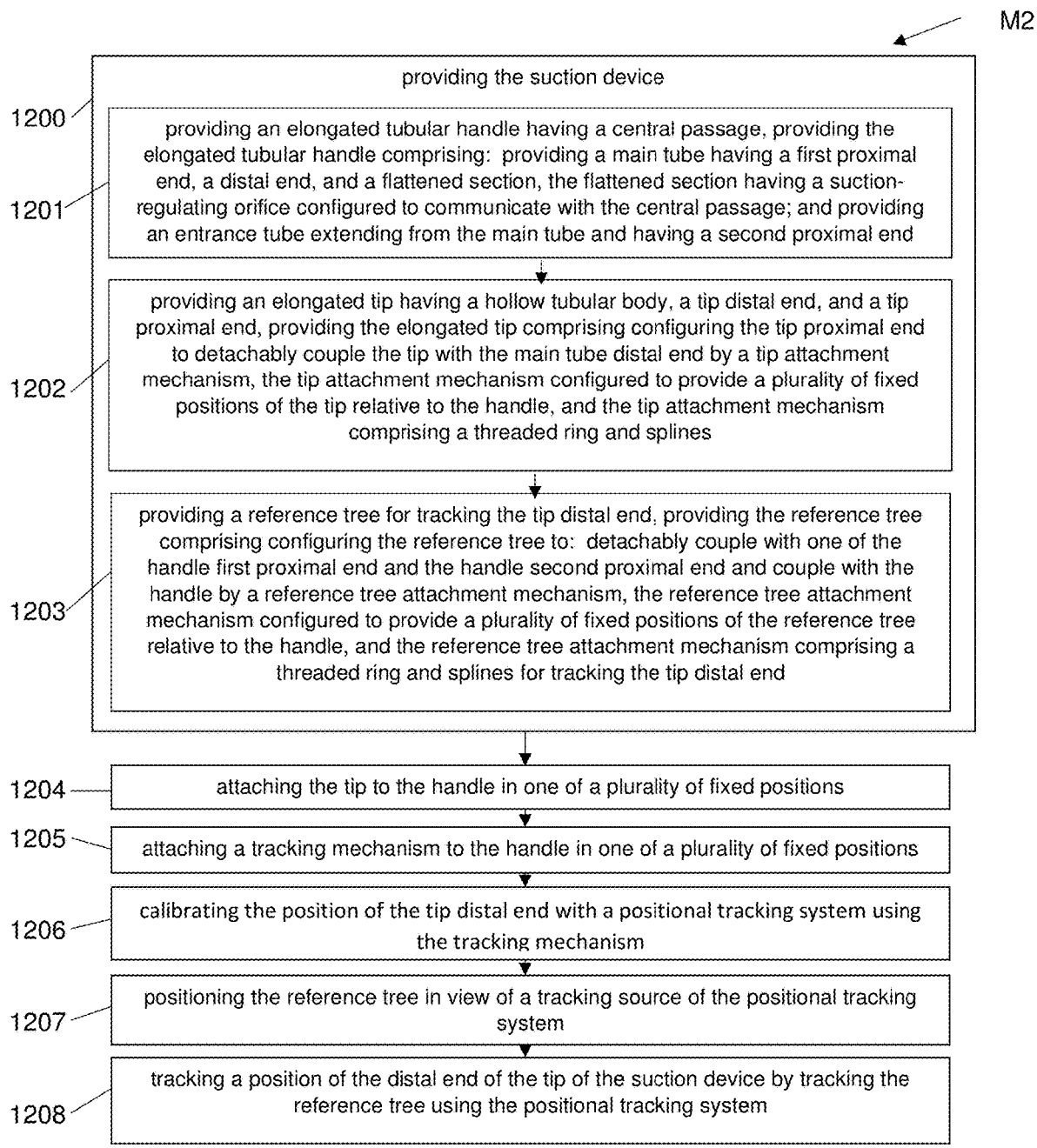
FIG. 12 is a flow diagram illustrating a method of tracking a suction device, in accordance with an embodiment of the present disclosure.

Referring to FIG. 12, this flow diagram illustrates a method M2 of tracking a suction device, e.g., a suction tool 300, in accordance with an embodiment of the present disclosure. The method M2 comprises: providing the suction device, e.g., a suction tool 300, as indicated by block 1200, providing the suction device comprising: providing an elongated tubular handle, e.g., a handle 310, having a central passage, providing the elongated tubular handle comprising: providing a main tube having a first proximal end, a distal end, and a flattened section, the flattened section having a suction-regulating orifice configured to communicate with the central passage; and providing an entrance tube extending from the main tube and having a second proximal end, as indicated by block 1201; providing an elongated tip, e.g., a tip 360, having a hollow tubular body, a tip distal end, and a tip proximal end, providing the elongated tip comprising configuring the tip proximal end to detachably couple the tip with the main tube distal end by a tip attachment mechanism, the tip attachment mechanism configured to provide a plurality of fixed positions of the tip relative to the handle, and the tip attachment mechanism comprising a threaded ring and splines, as indicated by block 1202; and providing a reference tree, e.g., a reference tree 370, for tracking the tip distal end, providing the reference tree comprising configuring the reference tree to: detachably couple with one of the handle first proximal end and the handle second proximal end and couple with the handle by a reference tree attachment mechanism, the reference tree attachment mechanism configured to provide a plurality of fixed positions of the reference tree relative to the handle, and the reference tree attachment mechanism comprising a threaded ring and splines for tracking the tip distal end, as indicated by block 1203; attaching the tip to the handle in one of a plurality of fixed positions, as indicated by block 1204; attaching a tracking mechanism to the handle in one of a plurality of fixed positions, as indicated by block 1205; calibrating the position of the tip distal end with a positional tracking system using the tracking mechanism, as indicated by block 1206; positioning the reference tree in view of a tracking source of the positional tracking system, as indicated by block 1207; and tracking a position of the distal end of the tip of the suction device by tracking the reference tree using the positional tracking system, as indicated by block 1208.

The specific embodiments above described have been shown by way of example. Understood is that these embodiments may be susceptible to various modifications and alternative forms. Further understood is that the claims are not intended to be limited to the particular forms disclosed, but rather to cover all modifications, equivalents, and alternatives falling within the spirit and scope of the present disclosure.

What is claimed:

1. A trackable suction device, the device comprising:
   an elongated tubular handle having a central passage, the elongated tubular handle comprising: a main tube having a first proximal end, a distal end, and a flattened section, the flattened section having a suction-regulating orifice configured to communicate with the central passage; and an entrance tube extending from the main tube and having a second proximal end;
   an elongated tip having a hollow tubular body, a tip distal end, and a tip proximal end, the tip proximal end configured to detachably couple the tip with the main tube distal end by a tip attachment mechanism, the tip attachment mechanism configured to provide a plurality of fixed positions of the tip relative to the handle, and the tip attachment mechanism comprising a threaded ring and splines; and
   a reference tree for tracking the tip of the distal end of the suction device, the reference tree configured to: detachably couple with one of the handle first proximal end and the handle second proximal end and couple with the handle by a reference tree attachment mechanism, the reference tree attachment mechanism configured to provide a plurality of fixed positions of the reference tree relative to the handle, and the reference tree attachment mechanism comprising a threaded ring and splines for tracking the tip of the distal end of the suction device;
   wherein the tip attachment mechanism further comprises a threaded semi-captive nut, the threaded semi-captive nut further comprises:
   a first internal thread configured to engage the tip proximal end;
   a nut seating position configured to provide free rotation of the nut when the nut is engaged with the tip proximal end through the first internal thread to prevent the semi-captive nut from slipping from the tip during assembly and disassembly of the tip; and
   a second internal thread with a larger diameter than the first internal thread configured to engage the handle.

2. The device of claim 1, wherein the main tube flattened section is disposed in a plane defined by the main tube and the entrance tube.

3. The device of claim 1, wherein at least one of the handle first proximal end and the handle second proximal end is configured to couple with at least one of the reference tree and a suction tube.

4. The device of claim 3, wherein the reference tree comprise a plurality of threads configured to couple the reference tree with at least one of the handle first proximal end and the handle second proximal end.

5. The device of claim 3, wherein the suction tube comprises a plurality of ribs configured to couple the suction tube with at least one of the handle first proximal end and the handle second proximal end.

6. The device of claim 1, wherein the entrance tube extends from the main tube at an angle in a range of less than approximately 90°.

7. The device of claim 1, wherein the handle orifice comprises a tear-shaped orifice.

8. The device of claim 1, wherein the tip attachment mechanism further comprises a plurality of complementary splines on the handle and the tip proximal end.

9. The device of claim 1, wherein the reference tree attachment mechanism further comprises at least one of: complementary splines on the handle and the reference tree; a threaded captive nut to attach the reference tree to the handle; and markers for an optical navigation system.

10. A method of providing a trackable suction device, the method comprising:
    providing an elongated tubular handle having a central passage, providing the elongated tubular handle comprising: providing a main tube having a first proximal end, a distal end, and a flattened section, the flattened section having a suction-regulating orifice configured to communicate with the central passage; and providing an entrance tube extending from the main tube and having a second proximal end;
    providing an elongated tip having a hollow tubular body, a tip distal end, and a tip proximal end, providing the elongated tip comprising configuring the tip proximal end to detachably couple the tip with the main tube distal end by a tip attachment mechanism, the tip attachment mechanism configured to provide a plurality of fixed positions of the tip relative to the handle, and the tip attachment mechanism comprising a threaded ring and splines; and
    providing a reference tree for tracking the tip of the distal end of the suction device, providing the reference tree comprising configuring the reference tree to: detachably couple with one of the handle first proximal end and the handle second proximal end and couple with the handle by a reference tree attachment mechanism, the reference tree attachment mechanism configured to provide a plurality of fixed positions of the reference tree relative to the handle, and the reference tree attachment mechanism comprising a threaded ring and splines for tracking the tip of the distal end of the suction device;
    wherein the tip attachment mechanism further comprises a threaded semi-captive nut, the threaded semi-captive nut further comprises:
    a first internal thread configured to engage the tip proximal end;

a nut seating position configured to provide free rotation of the nut when the nut is engaged with the tip proximal end through the first internal thread to prevent the semi-captive nut from slipping from the tip during assembly and disassembly of the tip; and a second internal thread with a larger diameter than the first internal thread configured to engage the handle.

11. The method of claim 10, wherein providing the elongated tip comprises disposing the main tube flattened section in a plane defined by the main tube and the entrance tube.

12. The method of claim 10, wherein providing the elongated tubular handle comprises configuring at least one of the handle first proximal end and the handle second proximal end to couple with at least one of the reference tree and a suction tube.

13. The method of claim 12, wherein configuring at least one of the handle first proximal end and the handle second proximal end to couple with the reference tree comprises configuring a plurality of threads to couple the reference tree with at least one of the handle first proximal end and the handle second proximal end.

14. The method of claim 12, wherein configuring at least one of the handle first proximal end and the handle second proximal end to couple with the suction tube comprises configuring a plurality of ribs to couple the suction tube with at least one of the handle first proximal end and the handle second proximal end.

15. The method of claim 10, wherein providing the entrance tube comprises providing the entrance tube extending from the main tube at an angle in a range of less than approximately 90°.

16. The method of claim 10, wherein providing the elongated tubular handle comprises providing the handle orifice with a tear-shaped orifice.

17. The method of claim 10, wherein the tip attachment mechanism further comprises a plurality of complementary splines on the handle and the tip proximal end.

\* \* \* \* \*